(12) United States Patent
Jung (10) Patent No.: US 11,376,047 B2
(45) Date of Patent: Jul. 5, 2022

(54) SPINAL CORRECTION DEVICE

(71) Applicant: CG BIO CO., LTD., Seongnam-si (KR)

(72) Inventor: Ui Su Jung, Seoul (KR)

(73) Assignee: CG Bio Co., Ltd., Seongnam-si (KR)

( * ) Notice: Subject to any disclaimer, the term of this patent is extended or adjusted under 35 U.S.C. 154(b) by 0 days.

(21) Appl. No.: 17/278,109

(22) PCT Filed: Sep. 20, 2019

(86) PCT No.: PCT/KR2019/012259
§ 371 (c)(1),
(2) Date: Mar. 19, 2021

(87) PCT Pub. No.: WO2020/060301
PCT Pub. Date: Mar. 26, 2020

(65) Prior Publication Data
US 2021/0346066 A1    Nov. 11, 2021

(30) Foreign Application Priority Data
Sep. 21, 2018 (KR) .................. 10-2018-0113976

(51) Int. Cl.
*A61B 17/70* (2006.01)

(52) U.S. Cl.
CPC ...... *A61B 17/7086* (2013.01); *A61B 17/7011* (2013.01); *A61B 17/7032* (2013.01); *A61B 17/7085* (2013.01)

(58) Field of Classification Search
CPC ........... A61B 17/7086; A61B 17/7085; A61B 17/7011; A61B 17/7032

USPC .................................. 606/250–279, 86 a
See application file for complete search history.

(56) References Cited

U.S. PATENT DOCUMENTS

| | | | |
|---|---|---|---|
| 8,425,531 | B2 | 4/2013 | Salemi |
| 8,460,308 | B2 | 6/2013 | Marino et al. |
| 9,289,251 | B2 | 3/2016 | Leroux |
| 9,743,958 | B2 | 8/2017 | Ishii et al. |

(Continued)

FOREIGN PATENT DOCUMENTS

| | | |
|---|---|---|
| KR | 10-2014-0037135 A | 3/2014 |
| KR | 10-1703003 B1 | 2/2017 |

OTHER PUBLICATIONS

International Search Report cited in PCT/KR2019/012259, dated Jan. 2, 2020, 2 pages.

*Primary Examiner* — Eduardo C Robert
*Assistant Examiner* — Tara Rose E Carter
(74) *Attorney, Agent, or Firm* — Rothwell, Figg, Ernst & Manbeck, P.C.

(57) ABSTRACT

The present invention provides a spinal correction device comprising: a pedicle screw comprising a seating part having a pair of first slits formed opposite to each other, and a screw part disposed at one side of the seating part so as to be implanted into a bone; an extender having a pair of second slits for guiding a rod so as to seat same in the seating part, and detachably fastened at one side thereof to the outer surface of the seating part; a reduction body detachably fastened to the other side of the extender; and a rod reducer arranged to pass through the reduction body and the extender so as to fix the rod placed in the pair of second slits by pressing the rod against the seating part.

6 Claims, 5 Drawing Sheets

(56) References Cited

U.S. PATENT DOCUMENTS

2012/0191144 A1* 7/2012 Peultier .............. A61B 17/7086
606/86 A
2018/0153593 A1* 6/2018 Goel .................. A61B 17/7086

* cited by examiner

SPINAL CORRECTION DEVICE

CROSS-REFERENCE TO RELATED APPLICATION

This application is a 35 U.S.C. 371 National Phase application from PCT/KR2019/012259, filed Sep. 20, 2019, which claims priority to and the benefit of Korean Patent Application No. 10-2018-0113976, filed on Sep. 21, 2018 the disclosure of which are incorporated herein by reference in their entirety.

TECHNICAL FIELD

The present invention relates to a spinal correction device having an improved structure.

BACKGROUND

Various treatment methods for spinal diseases have been developed, and among them, there is a direct treatment method for correcting the spine by attaching a separate fixing device to the damaged vertebrae.

For example, a plurality of pedicle screws are implanted by spacing apart at predetermined intervals in the spine, and after a rod modified in the form of a spine to be corrected is placed on the upper side of the pedicle screw, the patient's spine is corrected to correspond to the shape of the rod, when the rod is seated in a seating groove on the upper side of the pedicle screw as an assembly aid structure called a pershader.

However, such a conventional pershader is a single-type assembly aid structure, the size thereof is difficult to miniaturize, and it cannot be adjusted depending on the distance from the rod to the spine according to the patient's body shape or spinal deformity, and thus, there is a problem in that a plurality of pershaders are necessary that have individual lengths.

In addition, since the conventional pershader has a slit formed for seating a rod on a pedicle screw and a rod reducer for bringing the rod and the pedicle screw close to each other is a single-type assembly aid structure, it is not easy to clean, and it can be the cause of an infection path that may occur in surgery.

SUMMARY OF THE INVENTION

The present invention has been devised to solve the above problems, and an object of the present invention is to provide a spinal correction device in which miniaturization and length variation can be implemented, and each part is separable.

In order to achieve the above object, the present invention provides a spinal correction device, including a pedicle screw including a seating part having a pair of first slits formed opposite to each other, and a screw part disposed at one side of the seating part so as to be implanted into a bone; an extender having a pair of second slits for guiding a rod so as to seat the same in the seating part, and detachably fastened at one side thereof to the outer surface of the seating part; a reduction body detachably fastened to the other side of the extender; and a rod reducer arranged to pass through the reduction body and the extender so as to fix the rod placed in the pair of second slits by pressing the rod against the seating part.

In addition, a first screw thread may be formed on an inner circumferential surface of the seating part, a second screw thread may be formed on an inner circumferential surface of the reduction body, and a third screw thread may be formed that meshes with the first screw thread or the second screw thread on an outer circumferential surface of the rod reducer.

In addition, a pair of first fastening grooves may be formed opposite to each other on an outer surface of the seating part, and the extender may include a pair of first fastening parts fastened to the pair of first fastening grooves, respectively.

In addition, each of the pair of first fastening parts may include a first fastening piece hinged to the extender in the central part to form a first hinge hole so as to be rotatable, in which a first hook is formed at one end that is fastened to any one of the pair of first fastening grooves; and a first elastic body having one end and the other end respectively connected to the other end of the first fastening piece and the outer surface of the extender so as to provide a fastening force to the first hook.

In addition, at the extender, a first hook groove may be formed in which the first hook may be inserted.

In addition, a second fastening groove may be formed on the outer surface of the extender, and the reduction body may include a pair of second fastening parts fastened to the second fastening groove.

In addition, each of the pair of second fastening parts may include a second fastening piece hinged to the reduction body in the central part to form a second hinge hole so as to be rotatable, wherein a second hook is formed at one end that is fastened to the second fastening groove; and a second elastic body having one end and the other end respectively connected to the other end of the second fastening piece and the outer surface of the reduction body so as to provide a fastening force to the second hook.

In addition, the second fastening groove may be formed in a ring shape along the outer surface of the extender, and the second hook may be formed in a curved shape so as to be fastened to a part of the second fastening groove.

Advantageous Effects

The present invention improves a fastening structure with a pedicle screw, and by improving the structure such that a pershader for fixing a rod to the pedicle screw is detachable, respectively, the spine correction device can be miniaturized, it is easy to change the length according to the spinal form, and it is possible to improve hygiene by separate washing.

DETAILED DESCRIPTION

Hereinafter, preferred exemplary embodiments of the present invention will be described in detail with reference to the accompanying drawings.

Unless otherwise defined, all terms in the present specification are the same as the general meanings of terms understood by those skilled in the art, and if the terms used in the present specification conflict with the general meanings of the terms, the definitions used in the present specification follow.

However, the invention to be described below is only for describing an exemplary embodiment of the present invention and is not for limiting the scope of rights of the present invention, and the reference numerals used identically throughout the specification denote the same constitutional elements.

Figure 1:
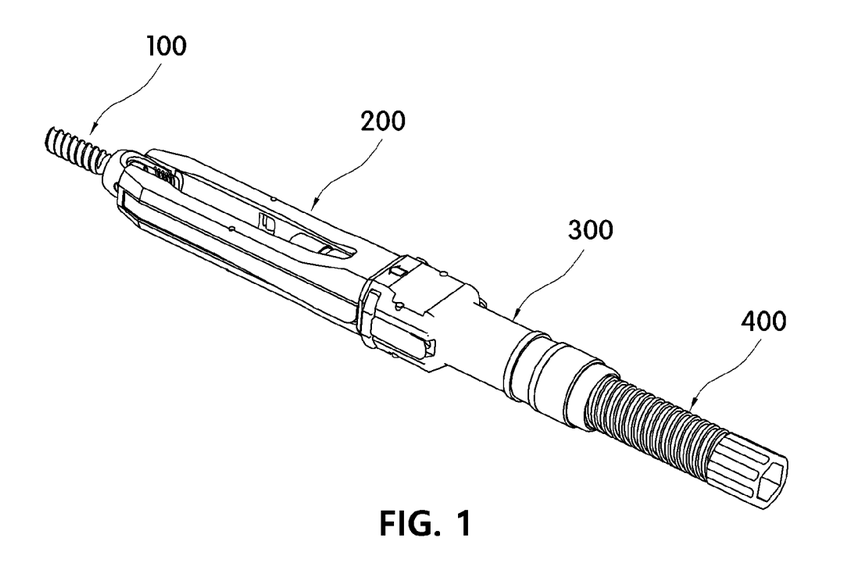
FIG. 1 is a perspective view of a spinal correction device according to an exemplary embodiment of the present invention.
Figure 2:
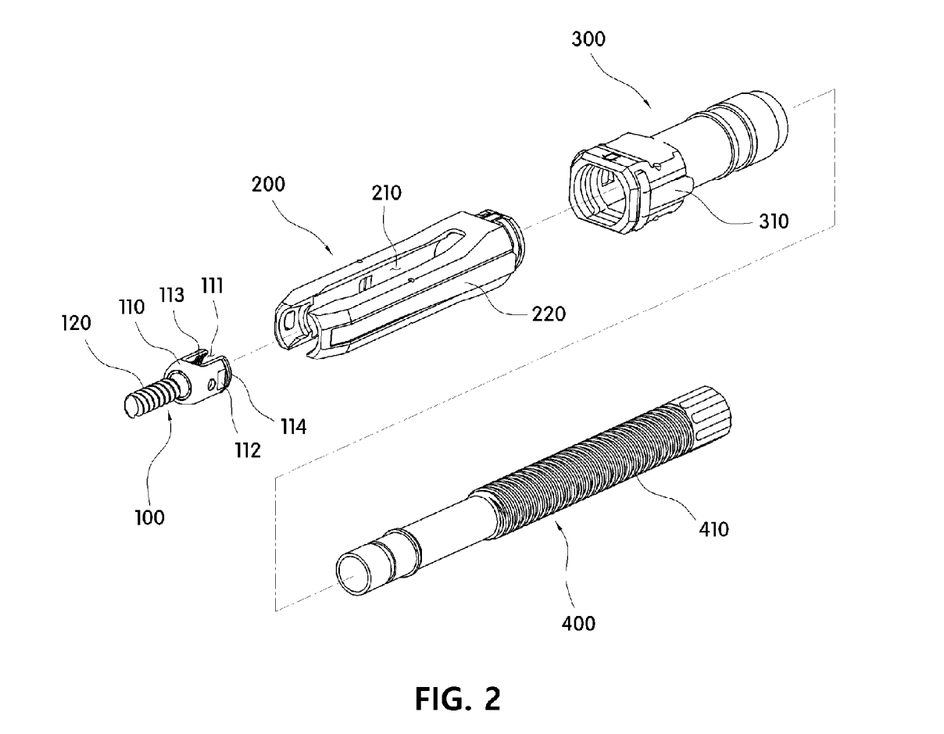
FIG. 2 is an exploded perspective view of a spinal correction device according to an exemplary embodiment of the present invention.
Figure 3:
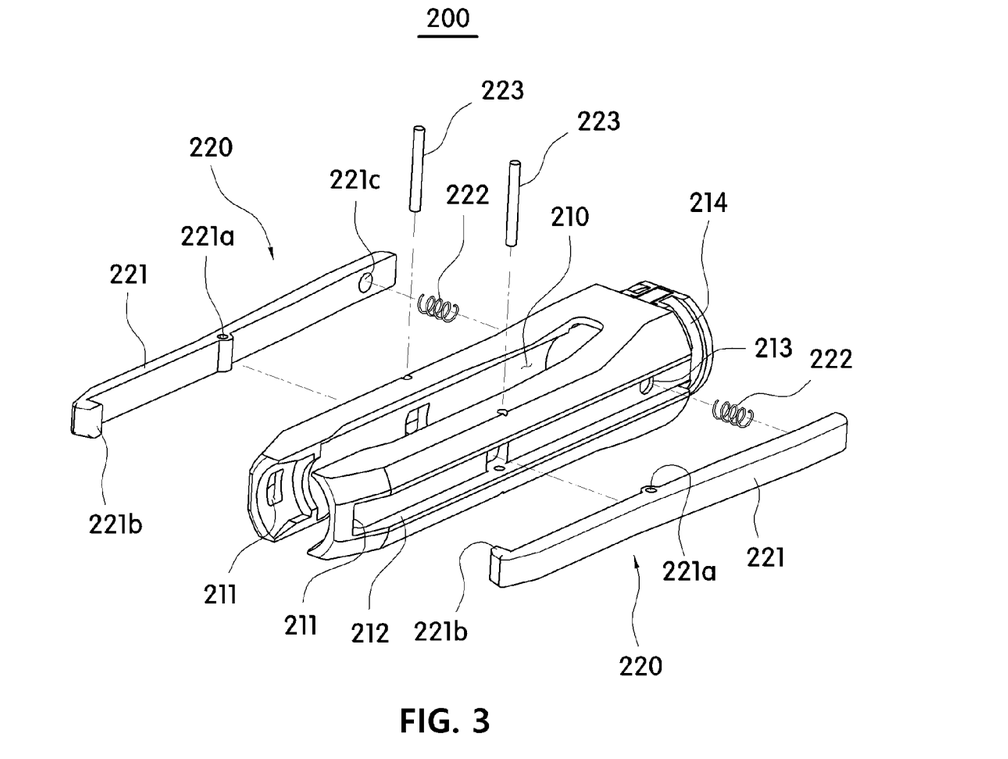
FIG. 3 is an exploded perspective view of an extender according to an exemplary embodiment of the present invention.
Figure 4:
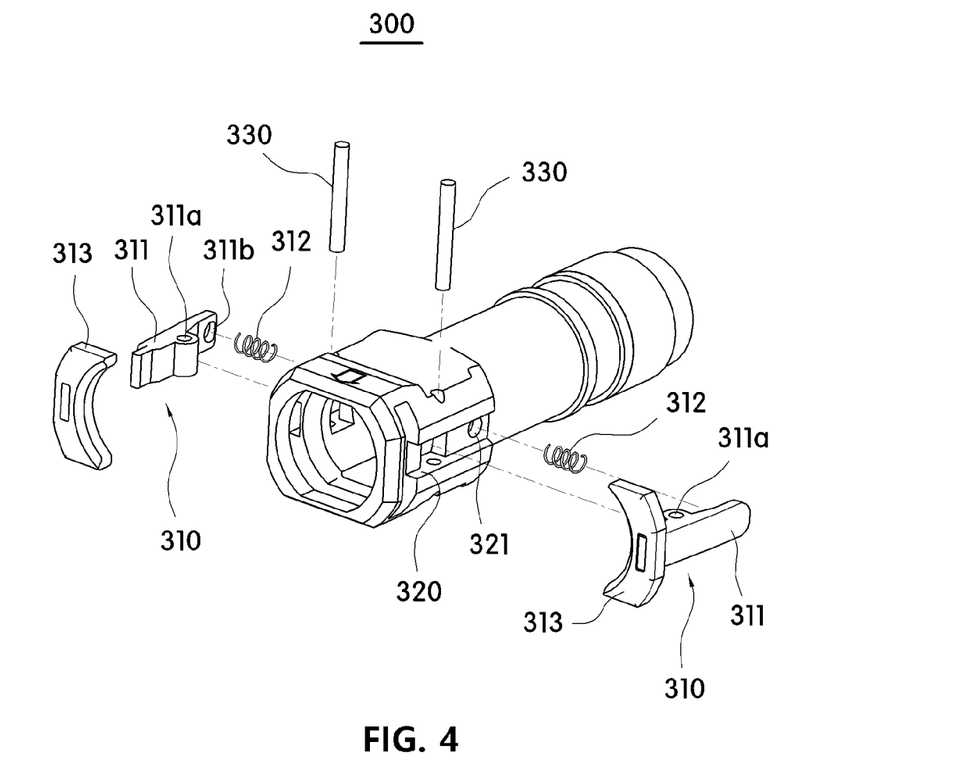
FIG. 4 is an exploded perspective view of a reduction body according to an exemplary embodiment of the present invention.
Figure 5:
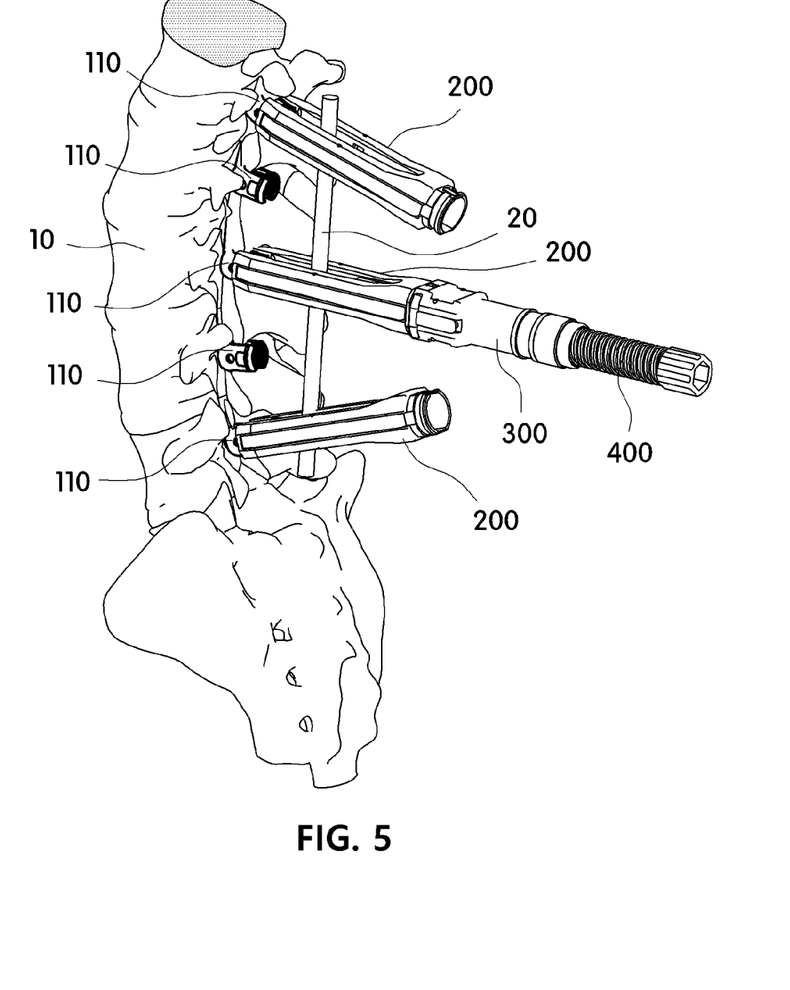
FIG. 5 is a usage condition diagram of a spinal correction device according to an exemplary embodiment of the present invention.

FIG. 1 is a perspective view of a spinal correction device according to an exemplary embodiment of the present invention, FIG. 2 is an exploded perspective view of a spinal correction device according to an exemplary embodiment of the present invention, FIG. 3 is an exploded perspective view of an extender according to an exemplary embodiment of the present invention, FIG. 4 is an exploded perspective view of a reduction body according to an exemplary embodiment of the present invention, and FIG. 5 is a usage condition diagram of a spinal correction device according to an exemplary embodiment of the present invention.

Referring to FIGS. 1 to 5, the spinal correction device according to an exemplary embodiment of the present invention may include a pedicle screw 100, an extender 200, a reduction body 300, and a rod reducer 400.

Herein, the extender 200 and the reduction body 300 may be formed with penetration parts in the longitudinal direction, respectively, to guide the rod reducer 400 to the pedicle screw 100.

In addition, the above-described pedicle screw 100, extender 200, reduction body 300, and/or rod reducer 400 may be made of any material having high biocompatibility, for example, it may be made of titanium, titanium alloy, or stainless steel.

The pedicle screw 100 is implanted in the spine 10, and the spine 10 correction may be achieved by seating the rod 20 manufactured in the shape of the spine 10 to be corrected.

Specifically, the pedicle screw 100 may include a seating portion 110 in which a pair of first slits 111 are formed opposite to each other, and a screw part 120 disposed at one side of the seating part 110 to be implanted in a bone.

In addition, a pair of first fastening grooves 112 for fastening with the extender 200, which will be described below, may be formed opposite to each other to the outer surface of the seating part 110.

In addition, a first screw thread 113 may be formed on the inner circumferential surface of the seating part 110. The first screw thread 113 may provide a pressing force for rotating the rod reducer 400, which will be described below, to press the rod 20 against the seating part 110.

Alternatively, the seating part 110 and the screw part 120 may be integrally formed, but may be formed in an assembly manner such that the screw part 120 is disposed by passing through the seating part 110.

In this case, a fixing nut for preventing the screw part 120 from being detached from the seating part 110 may be disposed inside the seating part 110, and the fixing nut may be threaded and fastened as the first thread screw thread 113.

In addition, a tapered part 114 that is formed to be inclined at a predetermined interval to the outside may be formed at a free end of the seating part 110, and by the tapered part 114, the coupling of the first fastening piece 221 to the first hook 221b, which will be described below, may be smoothly implemented.

The extender 200 is a constitutional component that extends the length of the pedicle screw 100, and may guide the rod 20 to be accurately seated inside the first slit 111 of the seating part 110.

Specifically, the extender 200 is formed with a pair of second slits 210 for guiding the rod 20 to be seated in the seating part 110, one side of which may be detachably fastened to the outer surface of the seating part 110.

The spacing of the second slit 210 may be formed to increase from both ends toward the center to facilitate the insertion of the rod 20 and to provide a wider working channel to the user.

That is, one side of the extender 200 may be fastened to the pedicle screw 100, and the other side may be fastened with a reduction body 300, which will be described below.

For fastening with the pedicle screw 100, the extender 200 may include a pair of first fastening parts 220 fastened to the pair of first fastening grooves 112 of the pedicle screw 100, respectively.

Herein, each of the pair of first fastening parts 220 may include a first fastening piece 221 and a first elastic body 222 to have the same function as clothespins, and thus, it may clamp the first fastening groove 112.

The first fastening piece 221 may be hinged to the extender 200 in the central part to form a first hinge hole 221a so as to be rotatable, and may be hinged to the extender 200 as a first pin 223.

In addition, a first hook 221b fastened to any one of the pair of first fastening grooves 112 may be formed at one end.

In addition, the first fastening piece 221 may be formed with a first arrangement groove 221c on which one end of the first elastic body 222 may be disposed at the other end.

The first elastic body 222 may be implemented as a coil spring or a plate spring, and one end and the other end thereof may be respectively connected to the other end of the first fastening piece 221 and the outer surface of the extender 200 so as to provide a fastening force to the first hook 221b.

That is, the first elastic body 222 may have a restoring force in a direction away from the outer surface of the extender 200 at the other end of the first fastening piece 221, and since the central part is hinged, one end of the first fastening piece 221 may be pressed against the outer surface of the extender 200.

Herein, in order to prevent the first hook 221b from colliding with the extender 200 when the fastening is released from the pedicle screw 100, a first hook groove 211, in which the first hook 221b may be inserted, may be formed at the extender 200.

In addition, the fastening part of the first fastening groove 112 and the first hook 221b may be formed to correspond to each other, and due to the coupling of the first fastening groove 112 and the first hook 221b, the direction of the first slit 111 of the pedicle screw 100 and the second slit 210 of the extender 200 is aligned to achieve a stable guide of the rod 20.

In addition, for miniaturization of the extender 200, a first recess groove 212 for arranging the first fastening piece 221 may be formed at a side surface of the extender 200. The first recess groove 212 may be formed in a shape corresponding to the first fastening piece 221.

In addition, the first hook groove 211 may be formed on the bottom surface of the first recessed groove 212, and a second arrangement groove 213 for arranging the other end of the first elastic body 222 may be formed.

In addition, a second fastening groove 214 for coupling with the reduction body 300, which will be described below, may be formed on the other outer surface of the extender 200.

In addition, since the extender 200 and the reduction body 300 do not require coupling in a specific direction, such as the coupling of the pedicle screw 100 and the extender 200, the second fastening groove 214 may be formed in a ring shape along the outer surface of the extender 200.

Herein, the ring shape may be continuously formed in a direction perpendicular to the length direction of the extender 200 on the outer surface of the extender 200, or may be formed to be partially disconnected.

The reduction body 300 is detachably fastened to the other side of the extender 200 and is a constitutional component capable of providing a pressing force while guiding the rod reducer 400, which will be described below.

A second screw thread (not illustrated) may be formed entirely or locally on the inner circumferential surface of the reduction body 300, and it is possible to impart a pressing force to a rod reducer 400, which will be described below, in the direction of the pedicle screw 100 by the second screw thread.

Since the reduction body 300 is detachably fastened to the extender 200, it may be manufactured in various lengths to correspond to the distance to the patient's spine 10, thereby enabling stable surgery.

For fastening with the extender 200, the reduction body 300 may include a pair of second fastening parts 310 fastened to the second fastening grooves 214.

The pair of second fastening parts 310 may include a second fastening piece 311 and a second elastic body 312, respectively, and may be functionally similar to the first fastening part 220 described above.

The second fastening piece 311 may be hinged to the reduction body 300 in the central part to form a second hinge hole 311a so as to be rotatable, and it may be hinged to the reduction body 300 as a second pin 330.

In addition, the second fastening piece 311 may have a second hook 313 fastened to the second fastening groove 214 at one end.

Herein, unlike the first hook 221b, the second hook 313 may be formed in a curved shape to be fastened to a part of the second fastening groove 214 such that it may clamp the extender 200 widely.

Accordingly, the second hook 313 may be integrally formed with the second fastening piece 311 or detachably formed on the second fastening piece 311.

In addition, the second fastening piece 311 may be formed with a third arrangement groove 311b in which one end of the second elastic body 312 is disposed at the other end.

The second elastic body 312 may be implemented as a coil spring or a plate spring, and one end and the other end thereof are respectively connected to the other end of the second fastening piece 311 and the outer surface of the reduction body 300, respectively, so as to provide a fastening force to the second hook 313.

That is, the second elastic body 312 may have a restoring force in a direction away from the outer surface of the extender 200 at the other end of the second fastening piece 221, and since the central part is hinged, one end of the second fastening piece 311 may be pressed against the second fastening groove 214.

In addition, for miniaturization of the reduction body 300, a second recess groove 320 for arranging the second fastening piece 221 may be formed on a side surface of the reduction body 300. The second recess groove 320 may be formed in a shape corresponding to the second fastening piece 311.

In addition, a fourth arrangement groove 321 may be formed on the bottom surface of the second recess groove 212 for arranging the other end of the second elastic body 222.

The rod reducer 400 may be arranged by passing through the reduction body 300 and the extender 200 in order to press and fix the rod 20 disposed in the pair of second slits 210 to the seating part 110.

For the pressing force, a third screw thread 410 that meshes with the first screw thread 113 or second screw thread (not illustrated) may be formed on the outer circumferential surface of the rod reducer 400.

That is, the rod reducer 400 may have a pressing force in a direction of the pedicle screw 100 due to rotation when the screw thread is fastened, and the pressing force passes through the reduction body 300 and the extender 200 to seat the rod 20, which is disposed in the first slit 111, in the first slit 111 of the seating part 110.

In summary, the present invention includes a structure in which the pedicle screw 100, the extender 200, the reduction body 300, and the rod reducer 400 may be each assembled such that the length of the spine 10 may be changed to suit the patient. Also, since it is easy to clean, it is possible to minimize the path of infection that may occur during surgery, and there is an advantage that miniaturization is possible.

As described above, those skilled in the art will be able to see that various changes and modifications can be made from the above description without departing from the technical spirit of the present invention, and the technical scope of the present invention is not limited to the contents described in the exemplary embodiments, but it should be determined by the scope of claims and its equivalent.

The invention claimed is:

1. A spinal correction device, comprising:
   a pedicle screw comprising a seating part having a pair of first slits formed opposite to each other, and a screw part disposed at one end of the seating part so as to be implanted into a bone;
   an extender having a pair of second slits for guiding a rod so as to seat the rod in the seating part, and detachably fastened at one end of the extender to an outer surface of the seating part;
   a reduction body detachably fastened to an opposite end of the extender; and
   a rod reducer arranged to pass through the reduction body and the extender so as to fix the rod placed in the pair of second slits by pressing the rod against the seating part,
   wherein a pair of first fastening grooves are formed opposite to each other on the outer surface of the seating part, and the extender comprises a pair of first fastening parts fastened to the pair of first fastening grooves, respectively,
   wherein each of the pair of first fastening parts comprises:
   a first fastening piece having a first and a second end, wherein the first fastening piece is hinged to a central part of the extender to form a first hinge hole so as to be pivotable, wherein a first hook is formed at the first end of the first fastening piece that is fastened to any one of the pair of first fastening grooves; and
   a first elastic body having a first end and a second end, wherein the first end of the elastic body is connected to the second end of the first fastening piece and the second end of the elastic body is connected to an outer surface of the extender so as to provide a fastening force to the first hook.

2. The spinal correction device of claim 1, wherein a first screw thread is formed on an inner circumferential surface of the seating part, a second screw thread is formed on an inner circumferential surface of the reduction body, and a third screw thread is formed that meshes with the first screw thread or the second screw thread on an outer circumferential surface of the rod reducer.

3. The spinal correction device of claim 1, wherein at the extender, a first hook groove is formed in which the first hook can be inserted.

4. The spinal correction device of claim 1, wherein a second fastening groove is formed on the outer surface of the extender, and the reduction body comprises a pair of second fastening parts fastened to the second fastening groove.

5. The spinal correction device of claim 4, wherein each of the pair of second fastening parts comprises:

a second fastening piece having a first end and a second end, wherein the second fastening piece is hinged to a central part of the reduction body to form a second hinge hole so as to be pivotable, wherein a second hook is formed at the first end of the second fastening piece that is fastened to the second fastening groove; and a second elastic body having a first end and a second end, wherein the first end of the elastic body is connected to the second end of the second fastening piece and the second end of the elastic body is connected to an outer surface of the reduction body so as to provide a fastening force to the second hook.

6. The spinal correction device of claim 5, wherein the second fastening groove is formed in a ring shape along the outer surface of the extender, and the second hook is formed in a curved shape so as to be fastened to a part of the second fastening groove.

* * * * *